United States Patent [19]

Ben-Simhon

[11] Patent Number: 5,451,223
[45] Date of Patent: * Sep. 19, 1995

[54] ELECTROSURGICAL INSTRUMENT

[76] Inventor: Haim Ben-Simhon, 78 - 280 McClellan Road, Nepean, Ontario, K2H 8P8, Canada

[ * ] Notice: The portion of the term of this patent subsequent to Feb. 4, 2009 has been disclaimed.

[21] Appl. No.: 280,587

[22] Filed: Jul. 26, 1994

Related U.S. Application Data

[63] Continuation of Ser. No. 780,333, Oct. 22, 1991, abandoned, which is a continuation-in-part of Ser. No. 594,704, Oct. 9, 1990, Pat. No. 5,085,657, which is a continuation-in-part of Ser. No. 475,145, Mar. 14, 1983, abandoned.

[51] Int. Cl.$^6$ ............................................. A61B 17/39
[52] U.S. Cl. ........................................ 606/42; 606/45; 606/49; 604/35
[58] Field of Search ......................... 606/41, 42, 45, 49; 604/22, 35

[56] References Cited

U.S. PATENT DOCUMENTS

| | | | |
|---|---|---|---|
| 2,828,747 | 4/1958 | August | 606/45 |
| 4,516,398 | 5/1985 | Wuchinich | 604/22 |
| 4,562,838 | 1/1986 | Walker | 606/49 |
| 4,719,914 | 1/1988 | Johnson | 606/49 X |
| 5,085,657 | 2/1992 | Ben-Simhon | 606/42 |

FOREIGN PATENT DOCUMENTS 438420 8/1974 U.S.S.R. ............................... 604/22

Primary Examiner—Lee S. Cohen
Attorney, Agent, or Firm—Martin J. Marcus

[57] ABSTRACT

A novel electrocutting/coagulating instrument is provided herein. The instrument includes a handle having a forward end and a rear end. A suction tube is secured to the handle and is adapted to be connected only to a source of suction. The suction tube has a forward end and a rear end, the rear end being connected to the handle, and also being connected to the source of suction, and the forward end of the tube projecting beyond the forward end of the handle. A manually-controllable, electrically-actuated cutting/coagulating blade electrode is operatively connected to the handle, a portion of the cutting/coagulating blade electrode projecting beyond the forward end of the handle. A lead is securely connected to the blade electrode and is adapted to be connected from a source of electricity to the cutting/coagulating blade electrode. A switch is provided to actuate the cutting/coagulating blade electrode, so that the suction tube provides a suction surrounding, and in close proximity to all portions of the cutting-/coagulating blade electrode. A connector is provided which has a leg and a pair of arms, the rear end of the suction tube being connected to one arm of the connector, the other arm of the connector being connected to a separate suction handle, and the leg of the connector being connected to a source of suction.

6 Claims, 6 Drawing Sheets

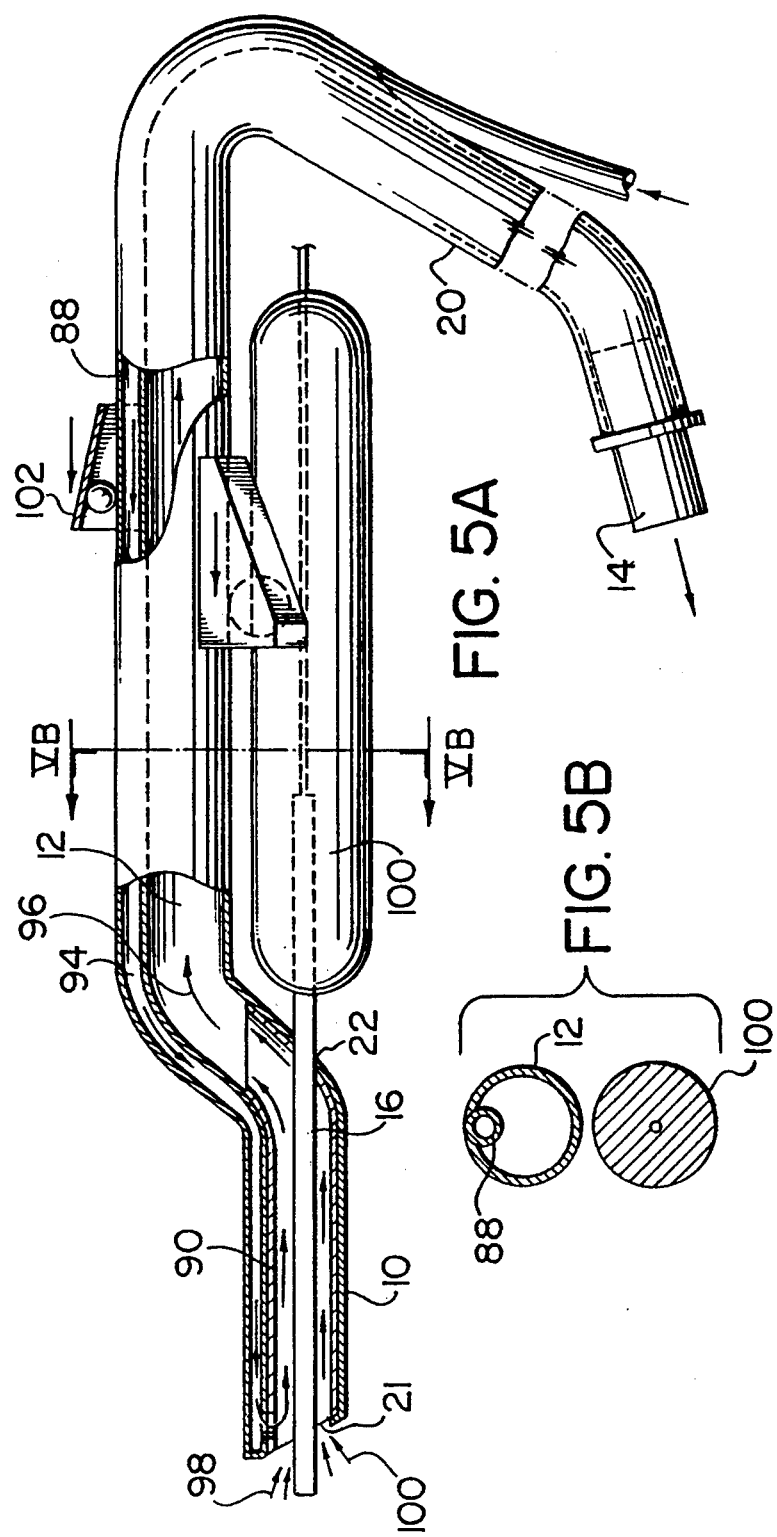

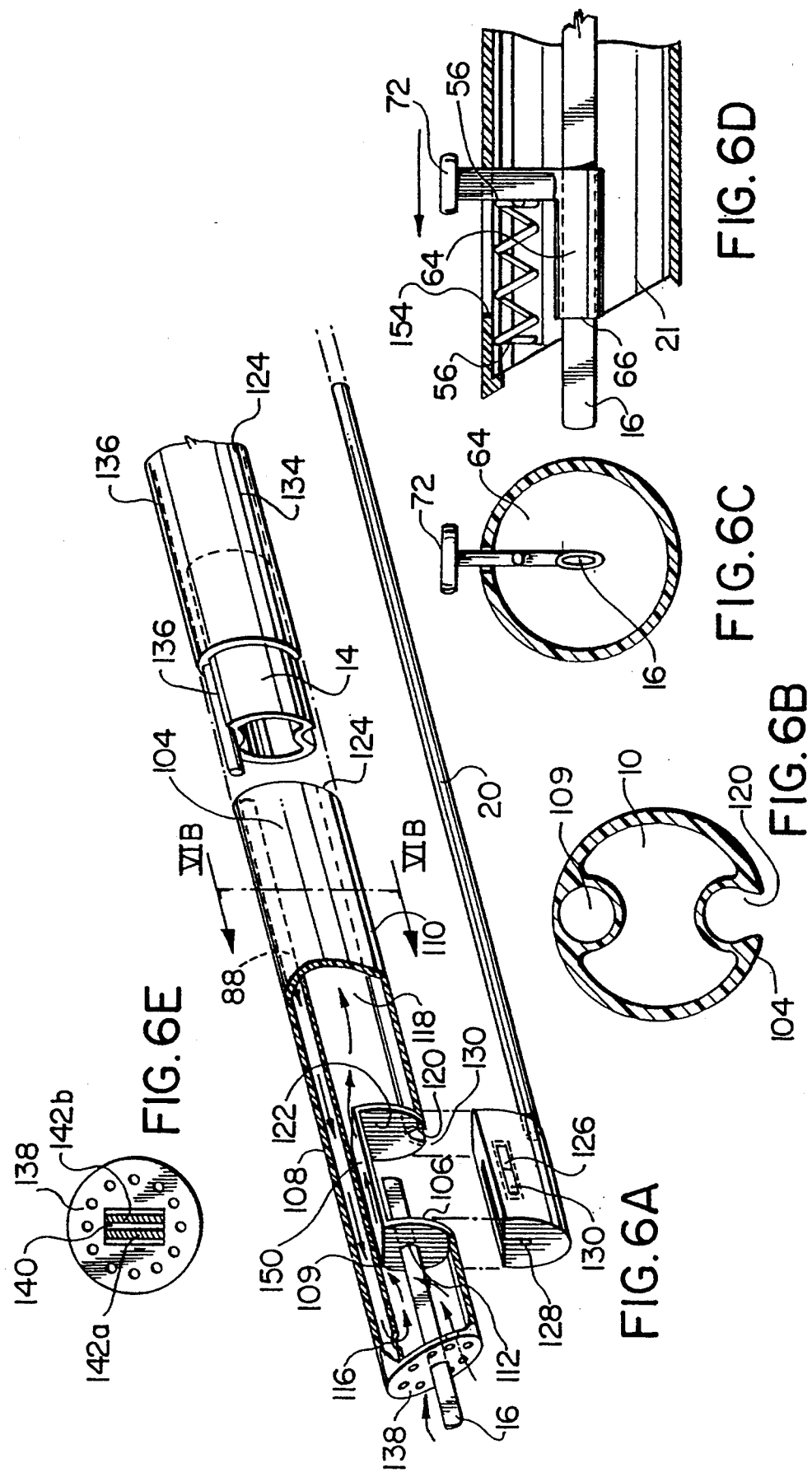

ELECTROSURGICAL INSTRUMENT

RELATED APPLICATION

This is a continuation of Application Ser. No. 07/780,333 filed Oct. 22, 1991, now abandoned which is a continuation-in-part of Application Ser. No. 07/594,704 filed Oct. 9, 1990, now U.S. Pat. No. 5,085,687, which in turn is a continuation-in-part of Application Ser. No. 475,145 filed Mar. 4, 1983, (now abandoned) the entire contents of all of which are incorporated herein by reference.

BACKGROUND OF THE INVENTION

1. Field of the Invention

The present intention relates to medical tools for general and specific surgery and more particularly to electrocutting/coagulation instruments which also include a cleaning device for the removal of ash formed in use.

2. Description of the Prior Art

Most surgical procedures now use an electrocutting-/coagulation instrument. Cutting with an electric blade or laser blade creates irritating smoke, and cuts blood vessels which bleed. This bleeding in turn disturbs its proper action.

Inhaling the smoke is a health hazard similar to that of air pollution and cigarette smoking. Also, with continuing exposure, it has an accumulative detrimental effect on the lungs. Therefore, providing an electrocutting instrument with the ability to remove such smoke health hazard, is an advantage.

Usually, the blood that results from cutting covers the line of the cutting and also impairs the quality of the electrocutting; thus the blood has to be removed before the electrocutting can be continued.

In the course of the cutting or coagulation with an electric (or laser) blade, ash is formed and sticks to the cutting edge of the blade. This ash has to be scraped off to restore the normal function of the instrument. Usually the surgeon has to stop the course of the surgical procedure and clean the tip with another instrument.

Every major surgical procedure in the chest, abdomen (or limbs) includes, as the first stage of the operation, opening the chest or abdominal wall by cutting through its layers. The main instrument used in this stage of the operation is the electrocutting-coagulation scalpel by which the different layers are cut by the main surgeon. The assistant in this stage holds a separate suction apparatus and/or sponges and wipes the blood.

However, the steady increase in time needed for the cutting and/or coagulation, which finally leads to the inevitable arrest of the instrument function, and the inevitable necessity to stop the course of surgery and to clean the instrument, are two major disadvantages of the existing forms of electrocutting blades.

One prior art electrosurgical instrument was that disclosed in U.S. Pat. No. 4,562,838, issued Jan. 7, 1986 to Walker. That patent provided an electrosurgical instrument including a hollow, elongated tube having an inner surface defining an internal longitudinally extending fluid conduit, the tube also having a mounting channel extending longitudinally along the length of the tube. The instrument included an active electrode. The instrument also included a nose piece mounted in the tube and holding the active electrode, the periphery of the nose piece being provided with at least one longitudinal flute which, together with the inner surface of the tube, defined a duct in fluid communication with the remainder of the fluid conduit, the duct being positioned to guide a fluid stream past the active electrode, the nose piece being constructed of an electrically nonconducting material. The instrument also included an electrical lead connected to the active electrode. Finally, the instrument included a light-transmitting cable slidably received within the mounting channel, with the light emitting end of the cable positioned adjacent to the active electrode to illuminate a region around the electrode. This patent did not solve the problem of removing the smoke, but only postponed the solution to the problem by diffusing the smoke into the operating room.

Another prior art electrosurgical instrument was that disclosed in U.S. Pat. No. 4,719,914 issued Jan. 19, 1988 to G. N. Johnson. That electrosurgical instrument included a hollow tubular member having an opening at one end adapted for connection by hollow tubing to a source of vacuum, and a ride opening adjacent to one end. The opposite end of the tubular member included a tapered hollow nose portion. An electrocauterizing blade was secured in, and had one end extending outward from, the end of the nose portion, and had the other end positioned inside the tubular member. Electric heating means were provided for the electrocauterizing blade including an electric lead extending through the tubular member and through the side opening for connection to a power source. The nose portion had a plurality of openings adjacent to the tapered surface thereof adapted to withdraw smoke from a surgical area being cut and cauterized by means of a cam connected to the tubular member open end. Means selectively controlled the application of vacuum through the nose portion openings were provided by means supported on the tubular member for selectively covering and uncovering the nose portion openings. While this patent attempted to use suction to remove smoke, the application of the suction was not at the optimum location with respect to the electrocauterizing blade.

Yet another prior art electrosurgical instrument was the electrocautery surgery apparatus disclosed in U.S. Pat. No. 4,919,129 patented Apr. 24, 1990 by Weber, Jr., et al. That apparatus included an elongated body having an electrical conductor positionable along a slidable path extending substantially therethrough toward a forward end thereof. The apparatus included connector means disposed near the forward end, the connector means being disposed to receive a conductive element therein for selective slidable positioning thereof relative to the forward end in response to slidable movement of the electrical conductor. Slider means were disposed on the body and were coupled to the electrical conductor for selectively altering the position thereof and of the connector means between forward and rearward positions thereof relative to the forward end. Circuit means were disposed in the body to be actuated by the electrical conductor for controlling the application of electrical signal thereto in response to the position of the electrical conductor along the slidable path thereof. The circuit means included an interlock switch operable in both the conductive state and the non-conductive state in response to the electrical conductor being positioned near the rearward position along the slidable path thereof. The interlock switch included auxiliary circuit means disposed in the body for grounding the electrical conductor during operation in the non-conductive state.

This patent did not address the problem of the removal of smoke from the area of the electrocautering apparatus.

SUMMARY OF THE INVENTION

(i) Aims of the Invention

An object of this invention is to provide means which could be mounted and/or removed easily from existing forms of electric or laser scalpels and which could provide means for the removal of smoke from the region of the electric or laser scalpel blades.

Another object of this invention is to provide a combined cutting-coagulation-suction apparatus, and/or combined cutting-suction apparatus and which provides means for the removal of smoke from the region of the electric or laser scalpel blades.

Applicant, in allowed copending Application Ser. No. 07/594,704, of which the present application is a continuation-in-part, provided several instruments involving novel combinations to solve such problems. These combinations were as follows:

In one embodiment of such instrument, the combination provided was a cutting-coagulation scalpel including a handle, an electrical lead to the handle, switch means on the handle, a blade electrode mounted at one end of the handle and connected to the electrical lead through the switch means on the handle for selectively activating and deactivating the blade electrode for cutting action or for coagulation action. A suction tube was removably mounted on the handle, the suction tube being connectable to a source of suction and comprising a modified L-shaped hard plastic transparent tube having a longitudinal arm and an angular arm, with an angle of about 135° between the longitudinal arm and the angular arm, the longitudinal arm having an open end and a back end, and being provided, at the open end, with an orifice, and, at the back end, with a thickened wall having a slot therethrough allowing penetration of the blade electrode therethrough. A soft plastic tube was also provided, which was connected to the angular arm. The soft plastic tube had a first set of hooks thereon, the first set of hooks each comprising two rings, one ring completely encircling the soft plastic tube, the other ring being constituted by two flexible arms to allow the handle to pop in between a gap between the two flexible arms thereby allowing the ring to be mounted on, and being positively attached to, the handle, and having a further set of hooks thereon for holding only the electric lead, each of the further set of hooks having a closed ring encircling the soft tube, and an open ring, the open ring being formed by two flexible arms, each of the further set of hooks being sized to allow the electrical lead of the cutting-coagulation scalpel to be engaged and disengaged in it. The blade electrode penetrated the modified L-shaped tube through the slot in the back end of the longitudinal arm, and was held in the center thereof by the thickened wall and protruded out of the orifice so that the blade electrode approached the cut and coagulated tissue areas. A tap was disposed on the suction tube, the tap being selectively operable to connect the suction tube to the source of suction, or to disconnect the suction tube from the source of suction.

In another embodiment of such instrument, the combination further included a cleaning device for the blade electrode. The blade electrode cleaning device included a metallic scraper element having a cylinder-like tip, the tip having razor-sharp edges encircling the blade electrode and having a slightly larger cross-section than the blade electrode, the tip being slidable on the blade electrode. The blade electrode had two slightly raised holding points thereon and was fixed to the scalpel handle and the slot in the back end of the scalpel handle and the slot in the back end of the modified L-shaped tube. A spring encircled the blade electrode around a portion of the blade electrode between one end of the handle and the holding points and was retained behind the holding points. An actuating lever was provided on the blade electrode, with a metallic strip connecting the tip and the lever. A portion of the metallic strip was slidable with respect to a portion of the blade electrode, the strip being integrally formed, at one end thereof, with a cylinder-like tip. Thus, when the lever was pushed towards the tip, it caused sliding of the tip in close proximity to the blade electrode, thereby to scrape the blade electrode and to cause compression of the spring. When the lever was released, the tip was restored to its initial position by spring energy.

In another embodiment of such patented instrument, the electrosurgical instrument included an insulated housing. A blade electrode was mounted at one end of the housing. An electrical unit was provided, which included switch means for selectively activating and deactivating the blade electrode. The electrical unit was disposed in the insulated housing. A suction channel was provided which had an orifice adjacent a tip of the blade electrode. A second channel was operatively connected to the suction channel for conveying flushing fluid to the suction channel. Scraping cleaning means were provided for scraping the blade electrode, the scraping cleaning means being carried by the blade electrode. The scraping cleaning means included manually-operable means for urging the scraping cleaning means to a forward position. The manually-operable means operated against spring means which urged the scraping cleaning means to a retracted, stored position. Release of the manually-operable means allowed the spring means to urge the scraping cleaning means from its forward position to its retracted stored position. In such embodiment the switch means was a two position switch for controlling cutting and coagulation procedures. The switch means was preferably provided on the housing.

In another embodiment of such instrument, the electrosurgical instrument included a handle having a forward end and a rear end. A suction tube having a forward end, a rear end, and side walls, was connected to the handle, the rear end of the suction tube being adapted to be connected to a source of suction, and the forward end of the suction tube projecting beyond the forward end of the handle. The suction tube included an aperture in a side wall of the forward end thereof. The forward end of the suction tube was flattened to an ellipsoidal cross-section in a region where it surrounded a blade electrode. The forward end of the suction tube terminated in a distal, obliquely-slanted outer face, and included an elliptically-shaped perforated membrane secured to the aperture. The membrane included a slot through which the blade electrode protruded. An electrical lead extended into the handle from the rear end thereof. A blade electrode was provided, the blade electrode having a forward end and a rear end, the rear end of the blade electrode being secured to the forward end of the handle, and being in electrical connection to the electrical lead. The forward end of the blade electrode projected through the aperture in the side wall of the forward end of the suction tube, and projected beyond the forward end of the suction tube. The blade electrode was completely surrounded by the suction tube. A switch was connected between the electrical lead and the blade electrode for selectively activating and deactivating the blade electrode. In such embodiment, the electrosurgical instrument included a thin, lightweight, flexible tube of soft rubber or silicone, the rear end of the suction tube being connected to the thin lightweight flexible tube, the thin lightweight flexible tube being adapted to be connected to a source of suction. The thin lightweight flexible tube had sufficient resiliency to allow flexibility at the rear end of the handle for ensuring convenient manipulation of the instrument.

In a further embodiment of such instrument, the electrosurgical instrument included a handle having a forward end, a rear end and a longitudinal axis. A suction tube having a forward end, a rear end, and sidewalls, was connected to the handle, the rear end of the suction tube being adapted to be connected to a source of suction. The forward end of the suction tube projected beyond the forward end of the handle, and extended along an imaginary extension of the longitudinal axis of the handle. The suction tube included an aperture in a side wall of the forward end thereof. An electrical lead extended into the handle from the rear end thereof. A blade electrode was provided, the blade electrode having a forward end, an intermediate portion and a rear end, a top edge of the rear end of the blade electrode was secured to the forward end of the handle, and was in electrical connection to the electrical lead. The intermediate portion of the blade electrode was disposed through the aperture in the side wall of the suction tube, the aperture being operatively associated with a rearwardly-extending ledge. The blade electrode was supported on the rearwardly-extending ledge. The forward end of the blade electrode projected beyond the forward end of the suction tube. The blade electrode was completely surrounded by the suction tube. A switch was connected between the electrical lead and the blade electrode for selectively activating and deactivating the blade electrode. Scraper cleaner means were provided for scraping the blade electrode, the scraper cleaner means being slidably mounted on the blade electrode. Manually-movable means were provided for moving the scraper cleaner means from an inactive position to a forward position in scraping sliding contact with the blade electrode, and back to the rearward, inactive position.

In one variant of this embodiment, the electrosurgical instrument included a thin, lightweight, flexible tube of soft rubber or silicone, the rear end of the suction tube being connected to the thin, lightweight, flexible tube. The thin, lightweight, flexible tube was adapted to be connected to a source of suction. The thin, lightweight, flexible tube had sufficient resiliency to allow flexibility at the rear end of the handle for ensuring convenient manipulation of the instrument.

In another variant of this embodiment, the electrosurgical instrument had a handle which included a longitudinally-extending slot within which the scraper cleaner means was adapted to slide. The scraper cleaner means included a scraper member having the same cross-section as the blade electrode but which was just slightly larger thereof. A rearwardly-extending connecting member enveloped the top edge of the blade electrode and extended into the longitudinally-extending slot in the handle. A lever was integral with, and upstood from, the rearwardly-extending connecting member and was slidable in the longitudinally-extending slot. A coil spring encircled a portion of the blade electrode, the coil spring being disposed between the forward end of the handle and a rear edge of the rearwardly-extending ledge.

In yet another variant of such embodiment, the electrosurgical instrument included an infusion tube only adapted to be connected to a source of flushing fluid, the infusion tube having a rear end, a forward end, and a side wall. The infusion tube ran parallel to, and was in contact with, the suction tube. The rear end of the infusion tube was connected to a source of flushing fluid. The forward end of the infusion tube was provided with an aperture in the side wall thereof connecting with an aligned aperture in an adjacent side wall of the suction tube.

While the above-described embodiment of applicant's above-identified co-pending application provided many advantages, it is a further objective of this invention to give the surgeon a practical, handy electrocutting or lasercutting apparatus which is provided with an assisting suction tube and flushing capability for the suction tube, the apparatus being able to be grasped like one grasps a pencil, and is thus being easy to manipulate while doing the main procedures of curdling and coagulating.

(ii) Statement of Invention

This invention provides an electrosurgical instrument comprising a suction tube formed of electrically non-conducting material having a longitudinal axis, a distal end adapted to be connected to a source of suction, and a frontal open end; a cutting/coagulating electrode having a frontal tip disposed within the suction tube, and extending parallel to a portion of the longitudinal axis thereof, and the frontal tip protruding from the frontal end of the suction tube, the electrode being adapted to be connected to a source of electrical power, the electrode being completely surrounded by, and lying completely within, the cross-section of the frontal open end of the suction tube, the tip of the protruding end of the electrode being sufficiently close to the frontal open end of the suction tube that, in operation, suction within the suction tube is sufficient for the efficient removal of smoke, blood and debris caused by the action of the electrode.

This invention also provides an electrosurgical device including a handle having a forward end and a rear end; an electrical lead entering the rear end of the handle; switch means in the form of a low profile, finger-actuatable electrical switch assembly to regulate the flow of current through the electrical lead; a cutting-/coagulation electrode within the handle, the cutting-/coagulating electrode being electrically connected to the electrical switch; a suction tube formed of electrically non-conducting material having a longitudinal axis, a forward open end and a rear end connected to the handle, the rear end of the suction tube being adapted to be connected to a source of suction, the forward end of the suction tube completely surrounding the cutting/coagulation electrode, the cutting/coagulation electrode extending parallel to a portion of the longitudinal axis of the suction tube; a liquid-conveying tube having a forward end and a rear end, the forward end communicating with the suction tube, the rear end being adapted to be connected to a source of liquid; and the cutting/coagulating electrode being completely surrounded by, and lying within, the cross-section of the forward open end of the suction tube, the electrode having a tip protruding from the forward open end, the tip of the protruding end of the electrode being sufficiently close to forward open end of the suction tube that, in operation, suction within the suction tube is sufficient for the efficient removal of smoke, blood and debris caused by the action of the electrode.

(iii) Other Feature of the Invention

In one feature of the invention, the electrosurgical instruction includes a liquid-conveying tube connected to the suction tube and means for controlling the flow of liquid within the liquid-conveying tube.

In another feature of the electrosurgical instrument embodiment of this invention, the cutting/coagulating electrode is encircled by the suction tube; and the cross-section of the frontal open end thereof forms an angle of up to 180° with the longitudinal axis of the suction tube; and including: means to control the extent of the protrusion of the cutting/coagulation electrode from the frontal end of the suction tube.

In yet another feature of the electrosurgical instrument of this invention, the handle is hollow; and the suction tube is provided with a perforated plate at its forward end, the perforated plate including a slot whereby the electrode projects beyond the perforated plate.

(iv) Generalized Description of the Invention

One feature of the present invention is the provision of a specifically constructed tube that may be mounted on, and removed easily from, the prior art existing forms of electric or laser scalpels. The invention therefore provides a combined cutting-coagulation-suction apparatus, and/or combined cutting-suction apparatus.

One advance made in the art of surgery is that this suction tube, which is light-weight and can easily be mounted on an electric scalpel, removes the irritating smoke, which is usually inhaled by the surgeon and his staff, immediately after its formation. In fact, it removes the smoke substantially, simultaneously with the cutting and prevents it from being inhaled by the operating staff.

Another advance, by the present invention, in the art of surgery, is that it removes the blood simultaneously with the electrocutting. This also applies when it is mounted on a simple scalpel with a sharp-edged blade. Removing the blood simultaneously with the cutting action spares the need to stop and wipe the blood or the need for an assistant for that purpose (the two actions are done by the surgeon who holds the combined instrument).

Another advance, by the present invention, is that, when mounted on an electric scalpel that is designed also to accomplish coagulation, it sucks the blood from the surrounding area of the cut-end of the blood vessel and enables proper coagulation of the bleeding vessel.

Another feature of the invention is the provision of an optional infusion tube that is connected to the suction tube, and is arranged to pour saline or sterile water into the suction tube in order constantly to flush the blood that might stick to the walls of the suction tube. Usually, the suction tubes do not block. However, in an especially long operation with an enlarged input of blood through the suction tube, the lumen of the suction tube could be narrowed by the clotted blood. The flushing will abolish this possibility completely.

This invention provides an instrument which frees the surgeon from stopping the course of surgery for cleaning the instrument. This invention provides a blade with a device that scrapes the ash from the tip by a single one cm movement of the index finger tip of the hand which holds the instrument. Because this is a very simple action, it could be performed during the course of procedure without stopping the main procedure. When this blade is mounted together with the suction device on the blade, the suction area will immediately suck the debris that is being scraped from the tip and prevent it from falling on the surgical field.

BRIEF DESCRIPTION OF THE DRAWINGS

In the accompanying drawings,

FIG. 5A and 5B is a side elevational view, partly in section and partly in phantom, which show, respectively, a flushing system for the electrocutting/coagulation scalpel handle of FIG. 1, and a cross-section thereof;

FIGS. 6A, 6B, 6C, 6D, and 6E collectively are an isometric view and sections, which show, respectively, a scalpel handle having a tube in which all the cutting-/coagulation-suction-flushing functions are included, a perforated plate for cleaning the blade, optional inverse construction of the tube, alternate perforated plate construction, and an optional cleaning tube;

DESCRIPTION OF PREFERRED EMBODIMENTS

Figure 1:
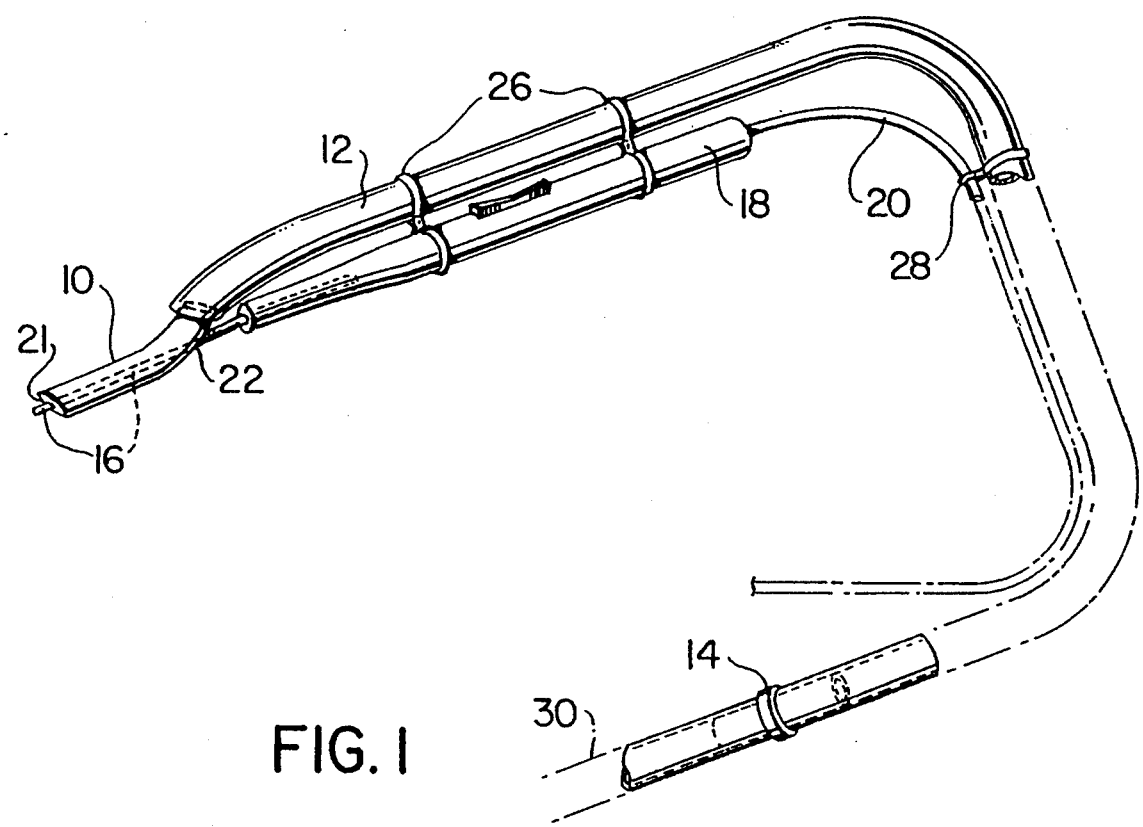
FIG. 1 is an isometric view showing one embodiment of a suction tube for an electrocutting/coagulation scalpel handle, constructed and operated in accordance with the principles of the present invention.
Figure 2A:
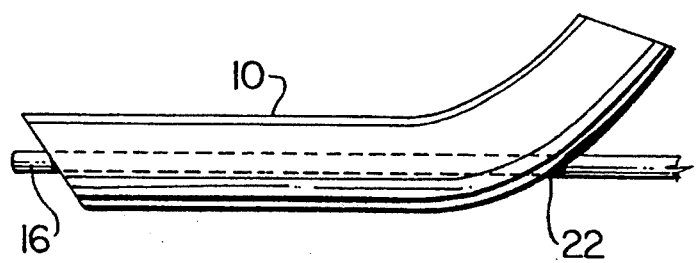
FIGS. 2A and 2B are side elevational views, partly in phantom, which show, respectively, penetration of a scalpel blade through a slot in the suction tube of FIG. 1, and an isometric view thereof.
Figure 2B:
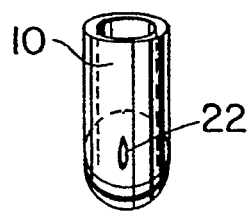

(i) Description of FIGS. 1, 2A and 2B

One embodiment of the invention consists of six parts, namely tube 10, tube 12, connector 14, blade 16, electric scalpel 18 with handle 18 and wire 20, which is attached to each other in the manner described in FIG. 1. Tube 10 is an essential element and is made of hollow, round, hard transparent plastic tube, shaped in the form of a modified letter "L", with an angle of about 135° between the horizontal and vertical arms of the "L". As seen in FIG. 2A, and FIG. 2B, the end of the horizontal arm is cut obliquely at a 45° angle to the plane of the horizontal arm to form an ellipse-shaped orifice 21. Through this orifice 21, the blade 16 of the electric scalpel 18 protrudes and approaches the tissue that is cut or the blood vessel that is coagulated. Through this orifice 21, the blood and smoke are sucked out of the tissue, to the inside of the tube 10.

The tube 12 is connected to another tube 30 by means of a plastic connector 14. Tube 30 leads to a negative pressure generating apparatus that provides the suction power. The tube 12 is indirectly connected to the handle 18 through tube 10, which is connected to blade 16, which in turn is connected to the handle 18.

The vacuum generating apparatus (not shown) attached to the tube 30 provides the suction.

The cutting blade 16 penetrates the horizontal arm of the modified L-shaped tube through the ellipsoid slot 22 (in the form complementary to the blade 161 adjacent the conjunction between the two tubes 10,12. The conjunction is thickened (see FIG. 2B) and the slot 22 is shaped exactly in the center of the tube 10, thus holding the blade 16 at the center of the round lumen of the tube 10 and enabling the blade 16 to protrude right in the center of the ellipsoidal orifice 21.

The back of the horizontal arm of the tube 10 is formed with thickened plastic (see FIG. 2B) whose purpose is to give strength to the central positioning of the cutting blade 16 in the lumen of the horizontal arm of the tube 10. An enlarged drawing is shown in FIG. 2B.

The vertical arm of the modified L-shaped tube 10 is a continuation of the lumen of the horizontal arm; it serves as a connector to tube 12.

Tube 12 is a hollow round tube made from soft rubber or silicone. It is thin, lightweight and flexible. It is attached to the handle of the electric scalpel 18 by two large plastic hooks 26 with an internal diameter which is the same as that of the handle of the electric scalpel 18, and with a shape as shown in FIG. 1.

Each hook 26 consists of two rings: one is full and encircles the tube 12. The other is partial and has two flexible arms with a spring quality that enables the handle of the scalpel 18 to "pop in" by forcing it through the gap between the two spring-like arms of the partial ring. Along the tube 12 are other hooks 28 (only one of which being shown) which are designed to hold the electric wire 20. These hooks 28 are the same as the hooks 26, but with smaller arms or "open rings" to fit the smaller diameter of the wire 20.

The wire 20 is connected to the distal part of the handle of the scalpel 18. At the other end, wire 20 is connected to the cutting-coagulation generator (not shown).

Figure 3B:
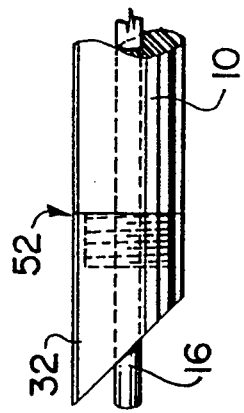
FIGS. 3A, 3B and 3C are side elevational views, partly in phantom, which show, respectively, an optional perforated orifice plate for use with the suction tube of the embodiment of FIG. 1, and a lock therefor, a cap-type of perforated plate, and a screw-cap type of perforated plate.
Figure 3C:
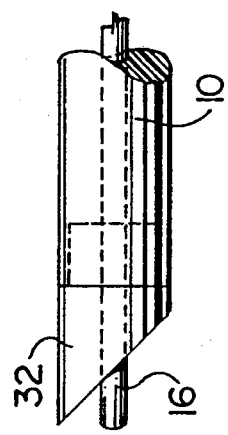
Figure 3A:
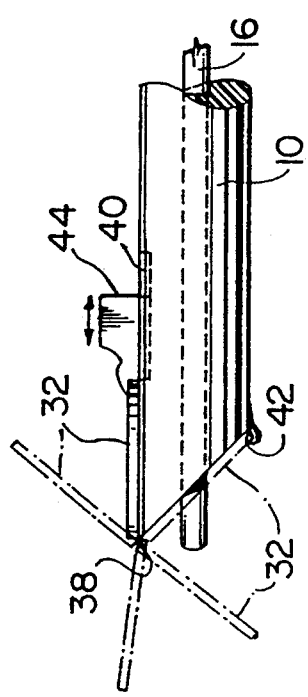

(ii) Description of FIGS. 3A, 3B, and 3C

Another embodiment of the invention is shown in FIGS. 3A, 3B and 3C. As seen therein, an ellipsoid perforated (with multiple perforations) plastic membrane 32 is mounted on the ellipsold orifice 21 of tube 10. The membrane 32 also has a slot 34 in its centre through which the electrocutting blade 16 protrudes.

This perforated membrane 32 is attached firmly to the ellipsoid orifice 21, causing a partial occlusion of the lumen (partial because of the perforations). The membrane could be removed from the orifice 21, all at the surgeon's choice.

There are several ways to give the membrane 32 and/or cover, and/or cap the ability to occlude or to be removed from the orifice 21 at the surgeon's will. In the embodiment shown in FIG. 3A, a plastic perforated plate, membrane 32, is attached to tube 10 in the upper pole of the ellipsoid orifice 21, by means of a segment of soft plastic 38. This segment 38 serves like a hinge around which the plate 32 can be rotated. The plate 32 may be an integral part of tube 10. Tube 10 will have two plastic locks, one, 40, on top of the "roof" of the tube 10 and the other, 42, on the lower pole of the ellipsoid orifice 21.

These plastic locks are designed to have a hook-shape which enables them to lock the plate 32, either parallel to the tube 10 by means of the lock in position 40, or closing on the ellipsoid orifice 21 by means of the lock in position 42. Additional hook-locks may be placed on both sides of the ellipsoid orifice 21 to add extra strength to the closure of the orifice 21, as an option of this invention.

Other possibilities of construction are a tight fitting cap-like perforated plate 32, which is fitted to cover firmly the distal part of the tube 10 (as shown in FIG. 3B); or one that could be screwed over tube 10 on threads 52 (as shown in FIG. 3C).

All three forms described above give the surgeon the possibility to open and/or close the orifice 21, as desired.

Figure 4A:
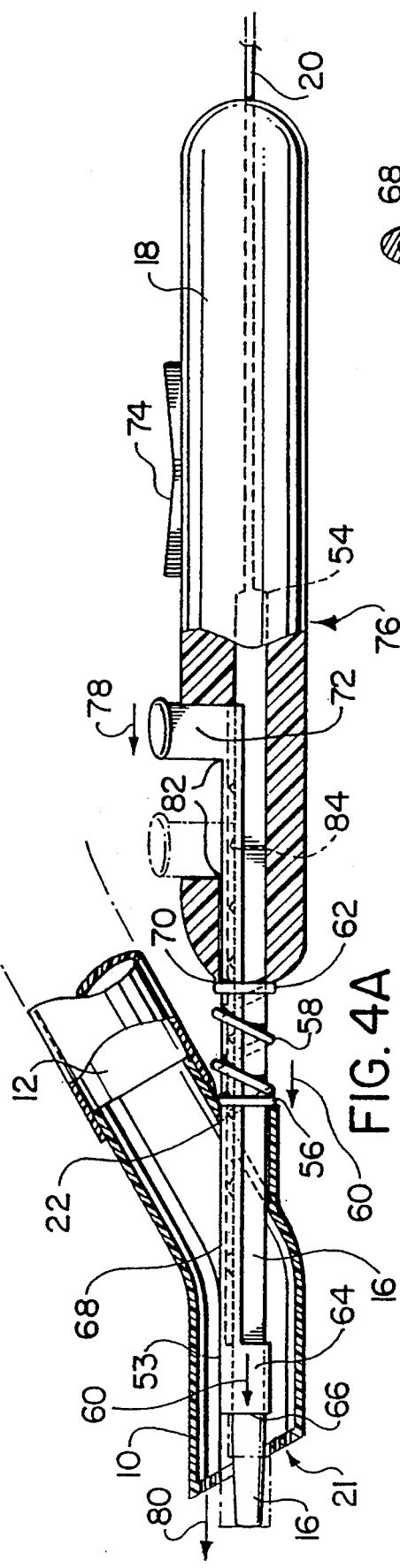
FIGS. 4A, and 4B is a central longitudinal cross-section in transverse section, which show, respectively, a cleaning device for the electrocutting/coagulation scalpel handle of the embodiment of FIG. 1, and a cross-section thereof.
Figure 4B:
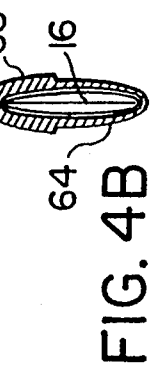

(iii) Description of FIGS. 4A and 4B

FIGS. 4A and 4B show a modified embodiment of this invention provided with a blade cleaning device. It will be appreciated that building a blade 16 with an "auto cleaning" mechanism which is easy to operate by movement of the index finger of a surgeon is very desirable. The cleaning device 53 is fitted to the blade 16 which is connected to the handle of the scalpel 18 at 54. The blade 16 protrudes through aperture 21. The blade 16 enters the lumen of the horizontal arm of tube 10 through a slot 22 in the thickened wall of the vertical arm of the tube 10. Blade 16 has two slightly raised holding points which prevent the spring 58, which encircles blade 16, from moving forward when the spring 58 is pushed in the direction of the arrow 60, by the ring 62 which has a slightly different diameter. Ring 62 is an integral part of the body of the cleaning device 53.

The cleaning device itself in the embodiment, as shown in FIG. 4A, is a long hollow metal Lube 64, about 1 cm long, that has the same ellipsoid cross-section as blade 16. However, the tube 64 is very slightly larger, to allow the blade 16 to fill the lumen of this ellipsoid cleaning tube 64. This tube 64 has a razor sharp leading edge 66 which lies very close to the blade 16 it encircles. The size of the gap between the tube 64 and the blade 16 is just big enough to allow sliding off the tube 64 along the tip of the blade 16.

Tube 64 is connected, by means of its upper wall, to a metallic, semicircular strip 68 which is, in fact, an integral part of tube 64. The semi-circular strip 68 lies over the upper part of blade 16, and "runs" along it, parallel and adjacent to blade 16. This strip 68 can slide over the blade 16, and also emerges from the plastic tube 10 through slot 22, at the back of the vertical arm of tube 10. At one point, strip 68 is attached to a ring 62, which encircles the blade 16 and can slide over it. Because ring 62 has a "rim" like a "doughnut", that covers the last ring of the spring 58, it can push and compress spring 58 if pushed in the direction of arrow 60. Two enlargements or holding points 56, in the blade 16 prevent the spring 58 from "running" forward. On the other hand, the compressed spring 58 can push ring 62 back by its stored energy.

The semi-circular strip 68 enters the handle of the scalpel 18 at point 70 and ends in a lever-shaped upstanding edge 72 that bulges out of the handle of the scalpel 18 near the on/off knob 74. The scalpel 18 is held like a pencil by its handle, i.e. the index finger pushes on knob 74 and the thumb on point 76.

There are other possibilities of mounting the retrieving mechanism of the device 53. The spring 58 may be placed around the semi-circular strip at segment 82, thus hiding it inside the handle of the scalpel 18. The holding point 56 of the blade 16 may be placed at point 84, the "doughnut" ring 62 of the semi-circular strip 68 in point 86 of the semi-circular strip 68 and the spring 58 encircling the blade 16 between point 84 and 86. This will also hide the retrieving part inside the handle of the scalpel 18. A similar cleaning device 53 mounted on bipolar forceps coagulation and/or bipolar coagulation suction apparatus is an option of this invention.

(iv) Description of FIGS. 5A and 5B

FIGS. 5A and 5B show a modified embodiment of this invention provided with an infusion device. As seen in FIG. 5A, an infusion tube 88 runs parallel to the suction tube 12. In fact, tube 10 and 12 may be provided as a double lumen tube, the small diameter lumen 88 being for the flow of flushing fluid and the large diameter lumen 12 being the suction tube itself. (See FIG. 5B). Tube 88 is connected to tube 10 through connector tube 90 at one end thereof. At the other end, tube 88 is connected to an infusion fluid bag (not shown).

The flow of the fluid in the tube 88 is caused by hydrostatic pressure which results from placing the infusion bag on a level higher than the level of connector 90 or 14. The rate of flow is regulated by means of a plastic cap 102 provided with a squeezing ball which controls the width of the lumen of the tube 88 and is placed close to the connection of the tube 88 with the fluid bag or bottle or on the part close to the tube 12. Connector 90 has a hollow lumen and is an integral part of tube 12.

The continuing whistle resulting from the continuous suction through the tube 10 is annoying to some surgeons. This may be abolished by placing an intravenous infusion type tap 102 on tube 12 that could narrow and close the lumen of the tube 12 by turning the wheel of the tap 103.

(v) Description of FIGS. 6A–6E

FIGS. 6A–6E show yet another embodiment of this invention, This alternative embodiment of this invention of cutting/coagulation-suction-flushing apparatus involves replacing the handle of the scalpel 18 (as shown in FIG. 1) and arranging the suction tube 12 and flushing (infusion) tube 88 in the position of the handle. This concept provides one tube which will include all functions of the apparatus, namely isolated connection to the electric wire 20 and off/on knob 74, the suction tube (10 and 12), and the flushing tube 88. FIGS. 6A–D illustrate the invention.

The tube 104 is formed of round, transparent plastic with a semi-cylindrical depression 106 towards the frontal edge of the tube 104. Thus, the tube 104 consists of an oblique or round orifice, leading to a hollow cylinder which continues as a semi-cylindrical lumen in the segment 108 of the depression 106 and then continues as a hollow round tube 134. The semi-circular plastic plate 109 that constitutes the "back" of the frontal cylinder 110 has an ellipsoid hole 112 through which the electric blade 16 is adapted to be inserted.

In the upper part of the tube 104, the flushing tube 88 is provided as a second small tube in which the flushing fluid flows and pours into the lumen of tube 104 near the orifice at point 116.

In the lower wall of the posterior cylinder 118 of tube 104, there is a longitudinal groove 120 which is elastic and is designed to house the electric cord 20. The groove 120 starts in the posterior wall of the depression, in plate 122, and ends at the back of the tube 104 at region 124. However, the groove may be continued into the following tube 134 that is connected by connector 14.

The electric unit 126 is made from plastic in a semi-cylindrical shape, similar to the shape of the depression 106. It is made in one piece with the electric cord 20 and is completely isolated except in point 128 where it is designed to grasp the posterior edge of blade 16. The unit 126 has an off/on apparatus and knob 130 on its side. The apparatus at point 128 that grasps the blade 16 in the unit 126 is a conventional apparatus and has four metal straps an a circular arrangement that spread forcefully when the blade 16, which has a larger diameter than that formed by the cross-section of the metal strips, penetrates between them when mounted on the unit 126.

The unit 126 fits exactly in the depression 106 in tube 104, and is kept in place by the blade 16 that penetrates the unit 126 in front and by the cord 20 in the groove 120 in the back. Plate 109 is especially thickened to add extra strength for holding the blade 16 and the unit 126.

Because of the suction area there will be no leakage from the hole 112 on plate 109 through which the blade 16 exits the tube 104. The connection in the rear is as follows: Tube 104 connects to another tube 134 through connector 14, and this in turn leads to the vacuum generating apparatus. Cord 20 remains as one unit until it connects to the electrocutting generator, this to maximize isolation of the current. The flushing tube 88 connects to the infusion tube 136 through a regular connector.

Arrows show fluid flowing in tube 88, pouring through point 116 and being sucked in the opposite direction in tube 104.

In another alternative embodiment of this invention, a rotatable, lock-hooked, perforated plate 138 with a slot 140 for the blade 16 is provided similar to that described in FIG. 3A. However, in this embodiment there is a modification that enables the plate 138 to clean the blade 16 from accumulating ash. The slot 140 has two sharp razor pieces 142a, 142b, in both sides of the slot 140, incorporated firmly into the plastic plate 138 (see FIG. 6e). When the plate 138 is rotated downward towards the orifice, blade 16 has to penetrate the slot 140. Since the slot 140 is very narrow, the razors 142a, 142b shave and push the debris inward to tube 104, where they are sucked away by the existing vacuum, as seen by the arrows in FIG. 6A.

A modification of this invention is a cleaning tube 64 encircling the blade 16 that has sharp edges 66, (as seen in FIG. 6D), and a lever 72 that extends outside the top of tube 104 through slot 154. Another modification of this invention is a retrieving mechansim as in FIG. 4D, provided with holding points 56 in FIG. 6D.

Figure 7:
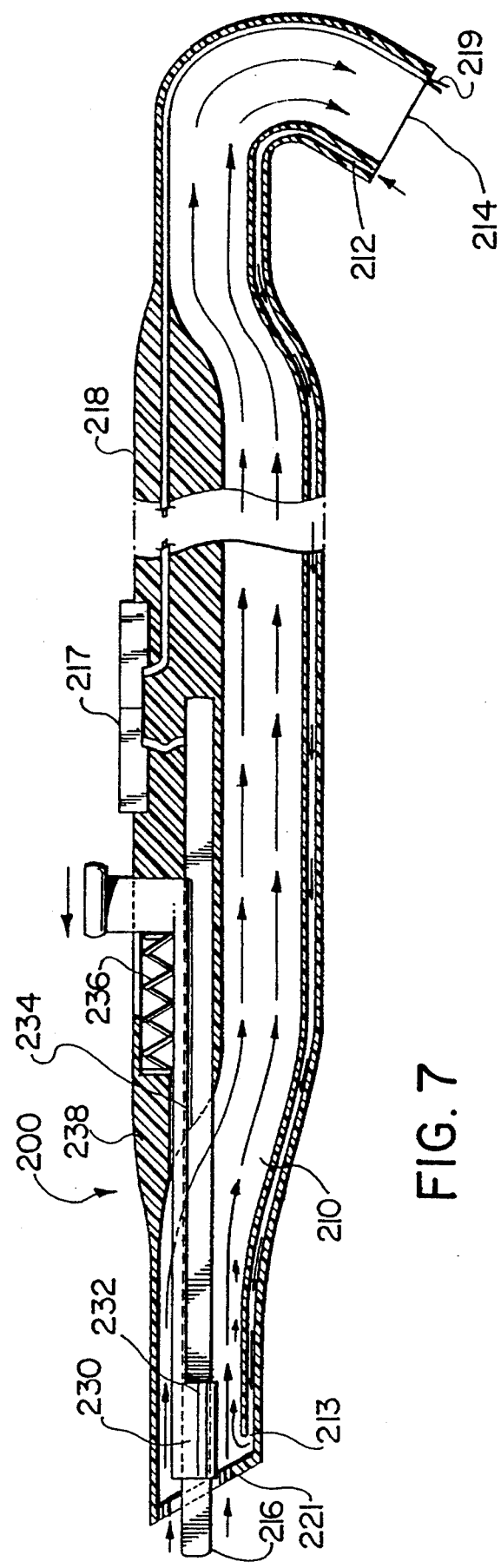
FIG. 7 is a central longitudinal cross-section of an alternative construction of the electrocutting/coagulation-suction apparatus of the invention.

(vi) Description of FIG. 7

A further embodiment is shown in FIG. 7. As shown in FIG. 7 an electrocutting instrument, shown generally as 200 includes the suction cleaning cauterizing and cutting functions all combined within a handle 218 of the instrument. The instrument 200 has an electrode blade 216 having an inner end connected to two position switch means 217 (to cut or cauterize) which is in turn connected to a source of R.F. energy through a supply ware 219.

A suction channel 210 having an orifice 221 adjacent the tip of blade 216, surrounds the blade 216 and extends under the handle 218. The suction channel 210 becomes a tube 212 at the trailing end of the handle where at is either formed of flexible plastic or is joined to flexible supply tubing by a connector at 214. A second and smaller channel and supply tube 213 provides flushing fluid to the first channel 210 adjacent the orifice 221.

The cleaning means 230 of this embodiment is a cylindrical member 232 carried by the blade 216 adjacent its forward end. The cylindrical member as similar to that of FIG. 4b and therefore need not be described in detail. A member 234 interconnects the cylindrical member 232 and a manually engageable portion 234 which extends out of the handle adjacent the switch assembly 217. A helical compression spring 236 is interposed between the manually-engageable portion 232 and stop means 238 provided in the handle of the instrument 200. The spring 236 is compressed when the cleaning element is moved forward and returns the cleaning element to a stored position when released.

Figure 8:
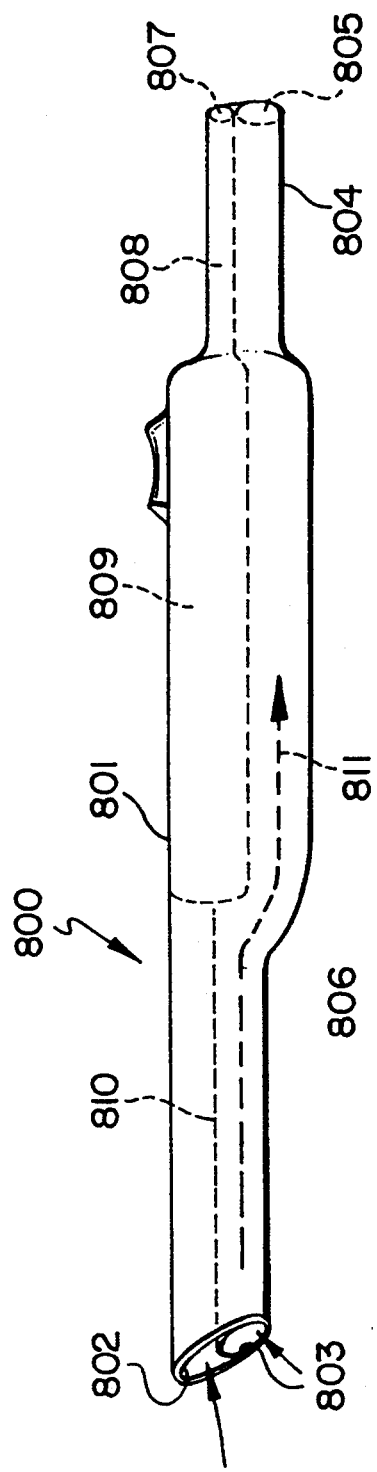
FIG. 8 is a schematic view of yet another alternative construction of the electrocutting/coagulation-suction instrument of the invention.

(vii) Description of FIG. 8

As seen in FIG. 8, the laser surgical instrument 800 includes a handle 801 having a forward end 802, generally as a downwardly sloping face 803, and a rear end 804. The rear end 804 is provided with an opening 805 which is connectable to a source of vacuum (not seen). This source of vacuum applies vacuum to the hollow longitudinally-extending base 806 of the handle 801. The rear end 804 is also provided with an aperture 807. Within the handle 801 is a laser source, i.e. a fiber optics mechanism 809. A lead 810 extends from a laser generator (not shown) through the aperture 807 to the fiber optics mechanism 809. The lead 810 is provided with switch means 811. While not shown, the handle may be provided with a flushing tube as described in FIGS. 5A and 5B. The output of the fibre optics mechanism 809 is a sharp laser beam 812 which is useful for surgery. The beam 812 is completely surrounded by the suction in base 806 as shown by arrow 813.

6) USE OF THE INVENTION

(i) Operation of Embodiment of FIGS. 1, 2A and 2B

The ellipsoid shape of the blade 16 and the slot 22 in the thickened "back" of the tube 10 is to prevent rotation of the blade 16 inside the lumen of the horizontal arm and, of course, to prevent rotation of the protruding part of the blade 16. Prevention of rotation is important because, when cutting, the sharper edge of the blade 16 has to be consistently opposite to the tissue that it cuts, otherwise the cut will not be sharp and straight.

Membrane 32 serves two purposes: One purpose of the membrane 32 is that, because it partially occludes the orifice 21, it enables application of a smaller negative pressure or suction power on the blood, smoke and tissue underneath, than without it. Another purpose is that, because it is firmly attached to the walls that form the orifice 21, and because of the central positioning of the slot 34 through which the blade 16 protrudes, extra strength is added to the central positioning and fixation of the blade 16.

Thus, when in use, the electrosurgical blade performs the cutting action, while the suction draws away substantially all the smoke in the area of the cut, since it substantially completely surrounds the electrocutting blade.

(ii) Operation of Embodiment of FIGS. 3 and 3A

The greater part of formed ash adheres to the part of the electric blade 16 that is in touch with the cut tissue. This latter part of ash forms an isolating barrier between the metallic blade 16 and the tissue it is supposed to cut. This barrier increases the resistance to the flow of current (and consequently of the heat) from the blade 16 to the tissue that is cut or coagulated, and consequently impairs the optimal cutting and/or coagulating function of the blade 16.

The amount of ash that adheres to the blade 16 is directly proportional to the amount of cutting or coagulating ("burning" in surgeons slang) that is being performed. As the ash accumulates on the blade 16, resulting in a growing layer of ash formed thereon, the resistance to the flow of current becomes proportionately greater. This necessitates a longer application of the blade 16 on the tissue in order to achieve the same cut or coagulation that would have been achieved if the blade was clean from ash. Finally, the layer becomes so thick that no current flows to the tissue and it neither cuts nor coagulates and the surgeon had to make a break in the procedure and clean the blade 16 by means of scraping out the ash with a sharp metal blade or the blade of a scissors. This cleaning restores the conductance of the surface of the electric blade 16 and consequently, the proper flow of electric current from the blade 16 to the tissue is restored, thus achieving the proper cutting and coagulation functions of the instrument.

The process of cutting through the layers by the primary surgeon consists of cutting with the electrocutting instrument and when a considerably-sized blood vessel is cut and needs to be coagulated, the main surgeon presses on the coagulation button and the electric blade 16 coagulates; of course, he has to wipe out or clean the blood as explained before. Thus, the process is one of alternating operations of cutting and coagulation by the same blade 16 which differs only by pressing on different buttons; each button releases current which results in the respective operation, namely either suction or coagulation.

Now, both operations, suction and/or coagulation contribute ash that clings to the blade 16 as explained before. Cleaning the blade 16 constitutes a break and/or deviation from the "natural" course of the operation, namely, cutting and coagulation and thus consumes time and interferes with the practicability of the procedure.

In this embodiment, the mode of operation of the electrosurgical blade is as described for FIGS. 1, 2A and 2B. However, for its blade cleaning facet, the mode of operation is as follows: the surgeon by his index finger pushes the lever 72 about one (1) cm in the direction of arrow 78. This results in a movement of 1 cm of the strip 68, of which lever 72 is an integral part. The movement of the strip 68 in the direction of arrow 78 (forward) pushes the tube 64 with its sharp leading edge 66 in the same direction (arrow 60), namely forward. The moving sharp edge 66 which lies intimately on the blade 16 shaves the debris from the tip of the blade 16 that was in touch with the burnt tissue and on which the ash accumulated; the ash accumulates only on the part that touches the cut tissue.

In other words, a small movement, e.g. about 1 cm, causes the leading edge 66 to pass over the tip of blade 16, shaving and flushing the debris off the blade 16, where the debris "meets" the suction area provided by tube 10. In other words, the negative pressure in the ellipsoid orifice 21 area of tube 10 sucks the debris (like a vacuum cleaner) in the direction towards tube 12 and prevents it from falling on the surgical field. Simultaneously, the pushing of the lever 72 causes compression of the spring 58 in the direction of arrow 60. Thus, the spring 58 is squeezed between ring 62 and the holding points 56 on the blade 16, which results in increasing the stored energy of the spring providing a retrieving mechanism.

Now, when the surgeon releases his index fingertip from the lever 72, the spring 58 pushes the whole device 53 with the cleaning tube 64 backwards to the resting position. This releases the tip of the blade 16 that was covered by tube 64 when the spring 58 was compressed when cleaning device 53 is in the active position) and now the tip is clean and ready for action again.

The great advantage of this arrangement is that the easy operation fingertip movement should encourage the surgeon to clean the edge more frequently than he does. He does not have to make a break in the flow of the procedure. Thus the blade 16 is kept constantly at its optimal quality of no debris, no increased resistance to the flow of the electric current. This will have a significant contribution to the fluency of the surgical procedure.

(iii) Operation of Embodiment of FIGS. 5A and 5B

The operation of cutting and coagulation and removal of ash is the same as previously described for FIGS. 1, 2A and 2B. However, for the additional feature of flushing, the mode of operation is as follows: the flushing fluid is constantly flowing in the direction of arrow 94 in tube 88; due to the hydrostatic pressure, and flows into tube 10 through the connector nozzle 90. The fluid spreads inside tube 10, and since there is a constant suction area in tube 10, it is immediately sucked in the direction of arrow 96, flushing the wall of the tube 10 from blood or debris. The flushing fluid cannot leak either through the ellipsoidal orifice 21 or through the slight gap that exists in slot 22 in the rear. This is due to the existence of air movement towards the tube 10 at both areas (arrows 98 and 100) that is caused by the constant negative pressure inside tube 10. It is clear that connector 90 can be placed in any point along tube 10 or 12.

(iv) Operation of Embodiment of FIGS. 6A–6E

The operation of cutting and coagulation and removing of smoke is the same as previously described for FIGS. 1, 2A and 2B. However, the additional mode of operation with this instrument is as follows: First the electric unit 126 is inserted into the depression 106, the cord 20 is inserted in the groove 120 of tube 104, then the blade 16 is inserted through the orifice 21 and through the hole 112 in plate 109 to the "blade grasper" at point 128, which is part of the electric unit 126. The on/off knob is on the right side of the instrument and is activated by the index finger of the hand which grasps the instrument like a pencil.

(v) Operation of Embodiment of FIG. 7

The operation of this embodiment is the same as for the embodiments of FIGS. 1, 2A, 2B and 4A. However, in this embodiment it will be appreciated that when in use as described above, suction is available at the tip of the instrument to remove smoke, blood and ash. The suction tube is cleaned by fluid drawn in from the fluid supply tube 213. The surgeon also has fingertip control of the blade cleaning element so that cutting and cauterizing can continue without delays previously encountered in such surgical procedures.

(vi) Operation of the Embodiment of FIG. 8

The cutting and/or coagulation, with laser-generated heat during surgical procedures creates ash from the burnt tissue in the line of the cut or from points that are coagulated. Part of this ash evaporates as smoke, and another part sticks to the tissue that is being cut.

In operation, once the laser generator is actuated, the laser beam is formed. The beam passes through the hollow forward portion of the instrument and passes out through the oblique front face. It is preferred that the forward portion be formed of a transparent material. The laser beam performs the cutting operation, and the suction which surrounds it removes the smoke.

In this embodiment, there is, of course, no need to include the blade-scraping feature.

7) CONCLUSION

In conclusion, the four parts of the disclosure describe different aspects of a major surgical instrument: the electrocutting-coagulation apparatus. Note that many combinations are possible in constructing the instrument, and these include:

(a) Electrocutting-coagulation-suction apparatus.

(b) Electrocutting-coagulation with built-in cleaning mechanism.

(c) Combination of the electrocutting-coagulation-suction apparatus with a built-in cleaning mechanism.

(d) A laser cutting-coagulation-cutting apparatus with or without a flushing system.

(e) The combination that includes all the above options namely: electrocutting-coagulation-suction apparatus with a built-in cleaning system for electric blade and built-in flushing system for suction tube.

It is important to note that this device has a primary function to cut and coagulate. The secondary actions of the suction, flushing and cleaning of the blade are only to assist or to clear the way for the fluent execution of the main function, namely cutting and coagulation and this whole combination as such constitutes a new original concept of the mode of operating the cutting-coagulation apparatus in surgical procedures.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

I claim:

1. An electrosurgical instrument comprising: a tube formed of plastic material, having a longitudinal axis, a distal end adapted to be connected to a source of suction, whereby said tube functions as a suction tube, and a frontal open end; a cutting/coagulating electrode disposed within said tube along said longitudinal axis thereof, said electrode being spaced from said tube at said frontal end, an end of said electrode protruding from said frontal end of said tube; said electrode being adapted to be connected to a source of electrical power; said electrode being completely surrounded by, and fully lying within, said frontal open end of said tube; said electrode having a tip at said end of said electrode which protrudes from said frontal open end of said tube, said tip being sufficiently close to said open frontal open end of said tube so that, in operation, suction within said tube is sufficient for the efficient removal of smoke, blood and debris caused by said electrode.

2. An electrosurgical instrument comprising: a suction tube formed of plastic, said tube having a longitudinal axis, said tube having a distal end which is adapted to be connected to a source of suction, and said tube having a frontal open end; a cutting/coagulating electrode having a frontal tip disposed within said suction tube and extending parallel to a portion of the longitudinal axis thereof, said electrode being spaced from said tube, said frontal tip protruding from said frontal open end of said suction tube, said electrode being adapted to be connected to a source of electrical power; said electrode being completely surrounded by, and lying completely within, said frontal open end of said suction tube; said frontal tip of said electrode being sufficiently close to said frontal open end of said suction tube so that, in operation, suction within said suction tube is sufficient for the efficient removal of smoke, blood and debris caused by said electrode.

3. An electrosurgical device including a handle having a forward end and a rear end; an electrical lead entering the rear end of said handle; a switch in the form of a low profile, finger-actuatable electrical switch assembly, adapted to regulate flow of current through said electrical lead; a cutting/coagulation electrode within said handle, said cutting/coagulating electrode being electrically connected to said electrical switch assembly; a suction tube formed of plastic having a longitudinal axis, a forward open end and a rear end connected to said handle, said rear end of said suction tube being adapted to be connected to a source of suction, said forward end of said suction tube completely surrounding said cutting/coagulation electrode, said cutting/coagulation electrode extending parallel to a portion of the longitudinal axis of said suction tube, said electrode being Spaced from said suction tube; a liquid-conveying tube having a forward end and a rear end, said forward end communicating with said suction tube, said rear end being adapted to be connected to a source of liquid; and said cutting/coagulating electrode being completely surrounded by, and lying completely within, the forward open end of said suction tube, said cutting/coagulating electrode having a tip protruding from said forward open end, said tip of said cutting/coagulating electrode being sufficiently close to said forward open end of said suction tube so that, in operation, suction within said suction tube is sufficient for the efficient removal of smoke, blood and debris caused by said electrode.

4. The electrosurgical device as claimed in claim 3 wherein: said handle is hollow; wherein said suction tube and said liquid-conveying tube are disposed within said hollow handle; and wherein said suction tube is provided with a perforated plate at its forward end, said perforated plate including a slot whereby said cutting/coagulating electrode projects through said slot beyond said perforated plate.

5. The electrosurgical instrument of claim 3 including: means to control the extent to which said tip of said cutting/coagulation electrode protrudes from said forward open end of said suction tube 6. The electrosurgical instrument of claim 3 including means for controlling flow of liquid within said liquid-conveying tube.

* * * * *

REEXAMINATION CERTIFICATE (3662nd)
United States Patent
Ben-Simhon

[11] B1 5,451,223
[45] Certificate Issued    *Nov. 3, 1998

[54] ELECTROSURGICAL INSTRUMENT

[76] Inventor: Haim Ben-Simhon, 78 - 280 McClellan Road, Nepean, Ontario, Canada, K2H 8P8

Reexamination Request:
No. 90/004,737, Aug. 15, 1997

Reexamination Certificate for:
Patent No.: 5,451,223
Issued: Sep. 19, 1995
Appl. No.: 280,587
Filed: Jul. 26, 1994

[ * ] Notice: The portion of the term of this patent subsequent to Feb. 4, 2009, has been disclaimed.

Related U.S. Application Data

[63] Continuation of Ser. No. 780,333, Oct. 22, 1991, abandoned, which is a continuation-in-part of Ser. No. 594,704, Oct. 9, 1990, Pat. No. 5,085,657, which is a continuation-in-part of Ser. No. 475,145, Mar. 14, 1983, abandoned.

[51] Int. Cl.$^6$ .................................................. A61B 17/39
[52] U.S. Cl. ........................ 606/42; 606/45; 606/49; 604/35

[56] References Cited

U.S. PATENT DOCUMENTS 2,102,270  12/1937  Hyams .
2,275,167  3/1942  Bierman .
3,595,239  7/1971  Petersen .
4,134,406  1/1979  Iglesias .
4,562,838  1/1986  Walker .

FOREIGN PATENT DOCUMENTS 942732  7/1982  U.S.S.R. .

*Primary Examiner*—Lee S. Cohen

[57]  ABSTRACT

A novel electrocutting/coagulating instrument is provided herein. The instrument includes a handle having a forward end and a rear end. A suction tube is secured to the handle and is adapted to be connected only to a source of suction. The suction tube has a forward end and a rear end, the rear end being connected to the handle, and also being connected to the source of suction, and the forward end of the tube projecting beyond the forward end of the handle. A manually-controllable, electrically-actuated cutting/coagulating blade electrode is operatively connected to the handle, a portion of the cutting/coagulating blade electrode projecting beyond the forward end of the handle. A lead is securely connected to the blade electrode and is adapted to be connected from a source of electricity to the cutting/coagulating blade electrode. A switch is provided to actuate the cutting/coagulating blade electrode, so that the suction tube provides a suction surrounding, and in close proximity to all portions of the cutting/coagulating blade electrode. A connector is provided which has a leg and a pair of arms, the rear end of the suction tube being connected to one arm of the connector, the other arm of the connector being connected to a separate suction handle, and the leg of the connector being connected to a source of suction.

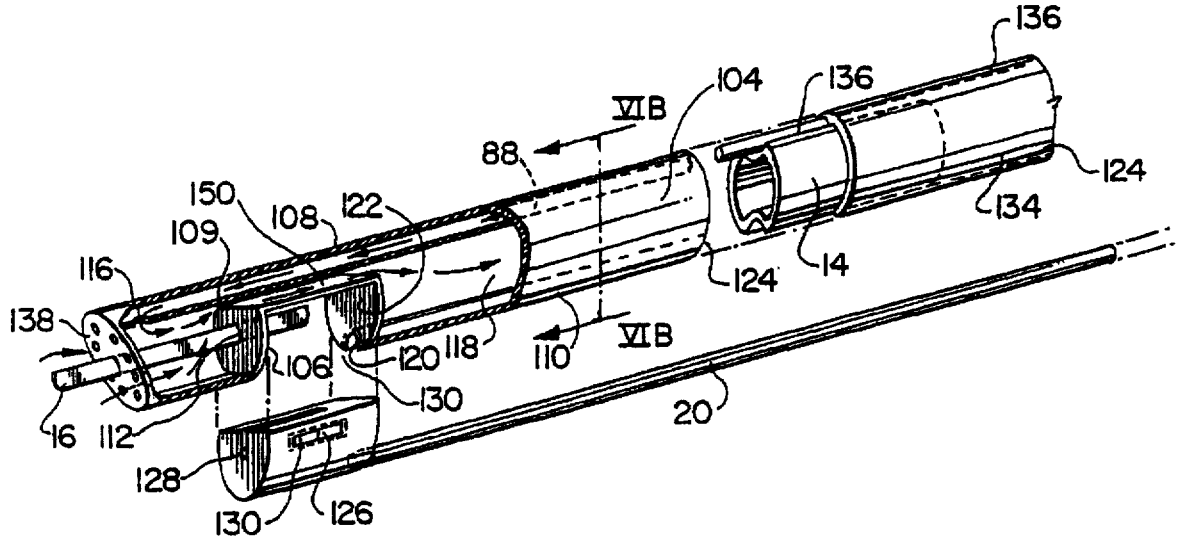

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–6 is confirmed.

* * * * *